United States Patent
Dormer

(10) Patent No.: US 6,277,148 B1
(45) Date of Patent: Aug. 21, 2001

(54) MIDDLE EAR MAGNET IMPLANT, ATTACHMENT DEVICE AND METHOD, AND TEST INSTRUMENT AND METHOD

(75) Inventor: Kenneth J. Dormer, Edmond, OK (US)

(73) Assignee: Soundtec, Inc., Oklahoma City, OK (US)

( * ) Notice: Subject to any disclaimer, the term of this patent is extended or adjusted under 35 U.S.C. 154(b) by 0 days.

(21) Appl. No.: 09/248,564

(22) Filed: Feb. 11, 1999

(51) Int. Cl.$^7$ ........................................... A61F 2/18
(52) U.S. Cl. .................................. 623/10; 600/25
(58) Field of Search ................ 623/10; 600/424, 600/559; 607/57, 137

(56) References Cited

U.S. PATENT DOCUMENTS

| | | |
|---|---|---|
| Re. 32,947 | 6/1989 | Dormer et al. . |
| 2,402,392 | 6/1946 | Goldschmidt . |
| 2,995,633 | 8/1961 | Puharich et al. . |

(List continued on next page.)

FOREIGN PATENT DOCUMENTS

| | | | |
|---|---|---|---|
| 833.809 | 3/1976 | (BE) . | |
| 1616149 | 1/1968 | (DE) . | |
| 2044870 | 9/1970 | (DE) . | |
| 0076069 | 4/1983 | (EP) . | |
| 553955 | 6/1943 | (GB) . | |
| 1421332 A1 | 9/1988 | (SU) | ........................ 623/10 |

OTHER PUBLICATIONS

International Publication No. WO 94/14376, Published Jul. 7, 1994, Cochlear Pty., Ltd., Telemetry System and Apparatus.

Richard L. Goode, M.D. and Theodore J. Glattke, Ph.D., Audition via Electromagnetic Induction, Arch Otolaryngol, vol. 98, pp. 23–26 (Jul. 1973).

Mendell Robinson, M.D. and Stephen D. Kasden, M.S., Bone Conduction Speech Discrimination, An indication of Cochlear Function in the Immediate Postoperative Period, Arch Otolaryngol, vol. 103, pp. 238–240 (Apr. 1977).

A. Tjellström, J. Lindström, O. Hallen, T. Albrektsson and P.I. Brönemark, Direct Bone Anchorage of External Hearing Aids, J. Biomed. Eng., vol. 5, pp. 59–63 (Jan. 1993).

B. Håkansson, A. Tjellström and U. Rosenhall, Hearing Thresholds With Direct Bone Conduction Versus Conventional Bone Conduction, Scand Audiol 13 (11 pages) (Mar. 1984).

*Primary Examiner*—David H. Willse
(74) *Attorney, Agent, or Firm*—McAfee & Taft

(57) ABSTRACT

An attachment device for a middle ear implant includes a first loop adapted to mount over structure in a middle ear. A second loop is connected to the first loop and adapted to mount over an object for use in the middle ear. A related method includes sliding a loop along at least part of a middle ear ossicle or prosthesis such that an object connected to the loop is disposed adjacent the ossicle or prosthesis. A method of testing for a magnet in a middle ear of a patient includes: inserting a coil at least into an outer ear canal of the patient adjacent the middle ear having the magnet; selectably aiming the coil relative to the middle ear; driving the coil with an alternating current signal at each selected aiming; obtaining at least one indication in response to driving the coil with an alternating current signal at each selected aiming; and determining a functional or positional characteristic of the magnet from the obtained indication. This method can be implemented with a plurality of coils. A related test instrument includes: at least one coil; and a connected handle to enable a user of the test instrument to insert the coil(s) into at least the outer ear canal and to direct electromagnetic signals at different directions relative to the middle ear.

17 Claims, 7 Drawing Sheets

U.S. PATENT DOCUMENTS

| | | |
|---|---|---|
| 3,209,081 | 9/1965 | Ducote et al. . |
| 3,384,090 | 5/1968 | Manfredi . |
| 3,594,514 | 7/1971 | Wingrove . |
| 3,712,962 | 1/1973 | Epley . |
| 3,722,003 | 3/1973 | Walchle . |
| 3,764,748 | 10/1973 | Branch et al. . |
| 3,870,832 | 3/1975 | Fredrickson . |
| 3,882,285 | 5/1975 | Nunley et al. . |
| 3,931,648 | 1/1976 | Shea, Jr. . |
| 4,052,754 | 10/1977 | Homsy . |
| 4,150,262 | 4/1979 | Omo . |
| 4,281,419 | 8/1981 | Treace . |
| 4,284,856 | 8/1981 | Hochmair et al. . |
| 4,292,693 | 10/1981 | Shea et al. . |
| 4,357,497 | 11/1982 | Hochmair et al. . |
| 4,419,995 | 12/1983 | Hochmair et al. . |
| 4,498,461 | 2/1985 | Hakansson . |
| 4,532,930 | 8/1985 | Crosby et al. . |
| 4,606,329 | 8/1986 | Hough . |
| 4,612,915 | 9/1986 | Hough et al. . |
| 4,624,672 | 11/1986 | Lenkauskas ............ 623/10 |
| 4,655,776 | 4/1987 | Lesinski ................ 623/10 |
| 4,776,322 | 10/1988 | Hough et al. . |
| 4,800,884 | 1/1989 | Heide et al. . |
| 4,817,607 | 4/1989 | Tatge . |
| 4,840,178 | 6/1989 | Heide et al. . |
| 4,871,364 | 10/1989 | Bays et al. . |
| 4,918,745 | 4/1990 | Hutchison . |
| 4,921,498 | 5/1990 | Bays et al. . |
| 4,936,305 | 6/1990 | Ashtiani et al. . |
| 5,015,225 | 5/1991 | Hough et al. . |
| 5,163,957 | 11/1992 | Sadé et al. . |
| 5,220,918 | 6/1993 | Heide et al. . |
| 5,259,032 | 11/1993 | Perkins et al. . |
| 5,306,299 | 4/1994 | Applebaum . |
| 5,338,287 | 8/1994 | Miller et al. . |
| 5,344,387 | 9/1994 | Lupin . |
| 5,360,388 | 11/1994 | Spindel et al. . |
| 5,425,104 | 6/1995 | Shennib . |
| 5,456,654 | 10/1995 | Ball . |
| 5,507,303 | 4/1996 | Kuzma . |
| 5,554,096 | 9/1996 | Ball . |
| 5,558,618 | 9/1996 | Maniglia . |
| 5,624,376 | 4/1997 | Ball et al. . |
| 5,741,316 | 4/1998 | Chen et al. . |
| 5,800,336 | 9/1998 | Ball et al. . |
| 5,993,376 | * 11/1999 | Kennedy ............ 600/25 |

* cited by examiner

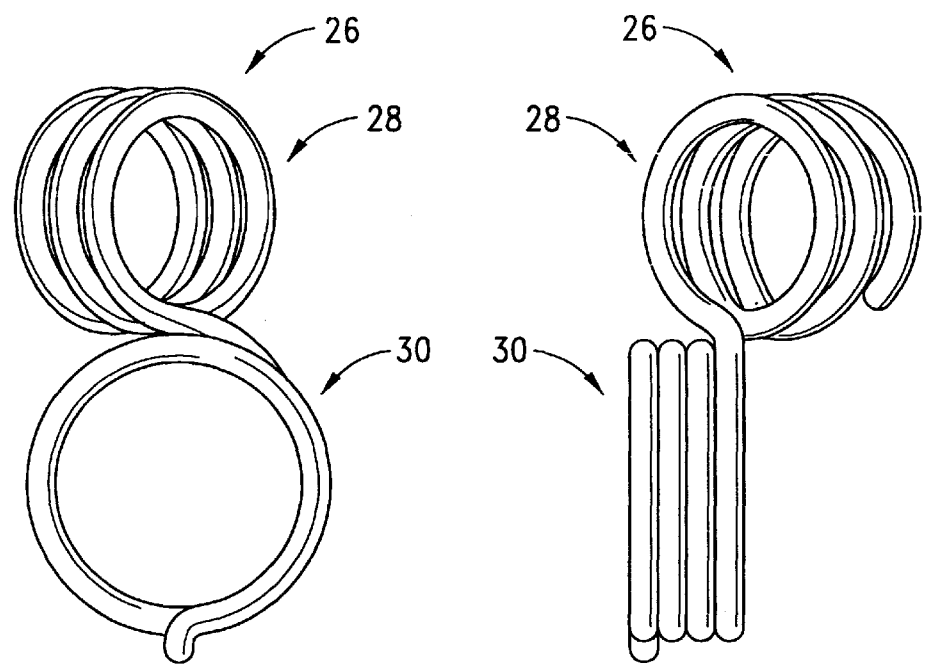
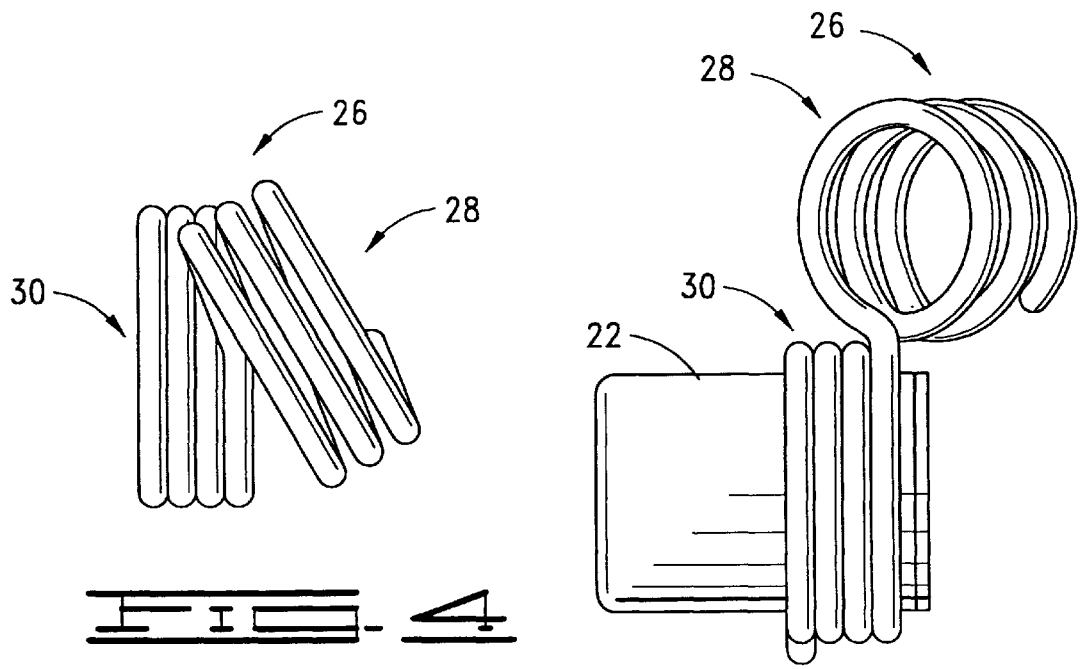

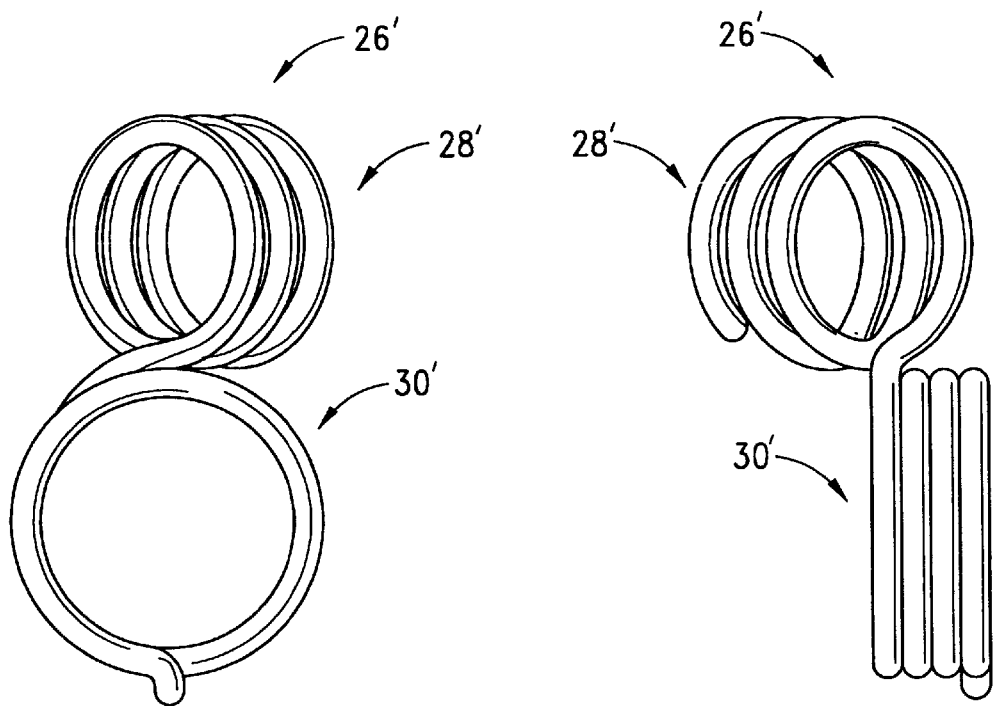
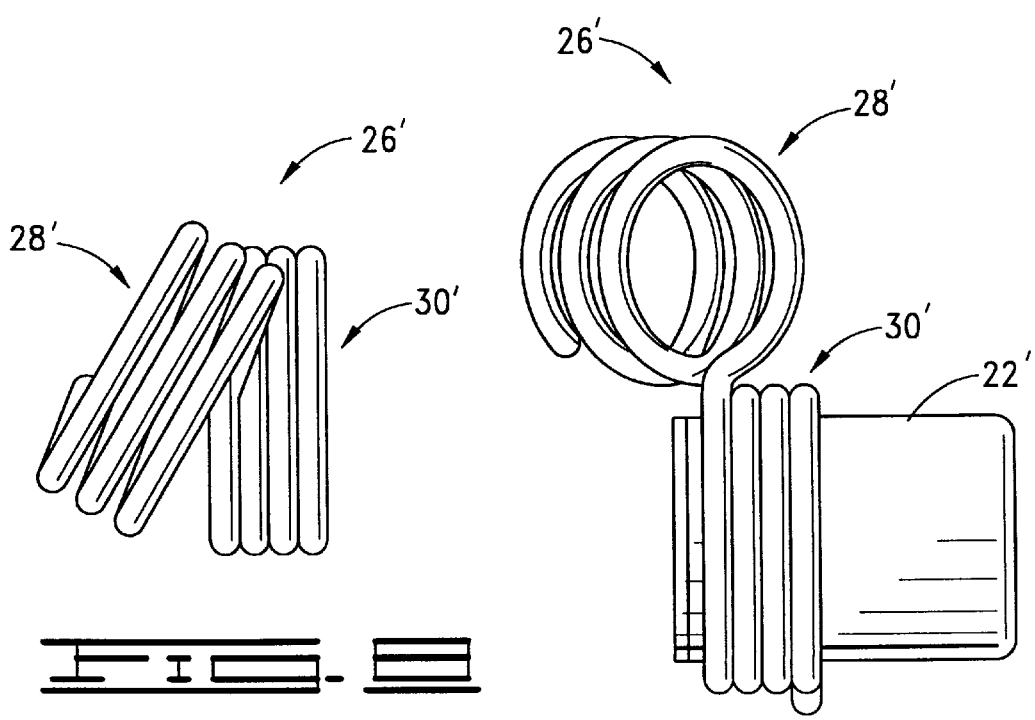

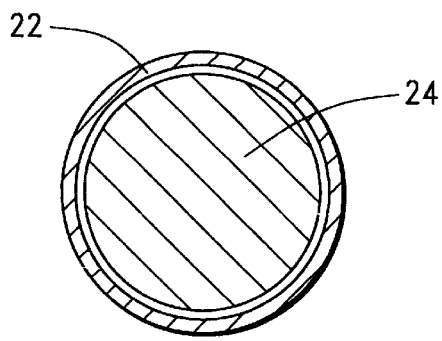
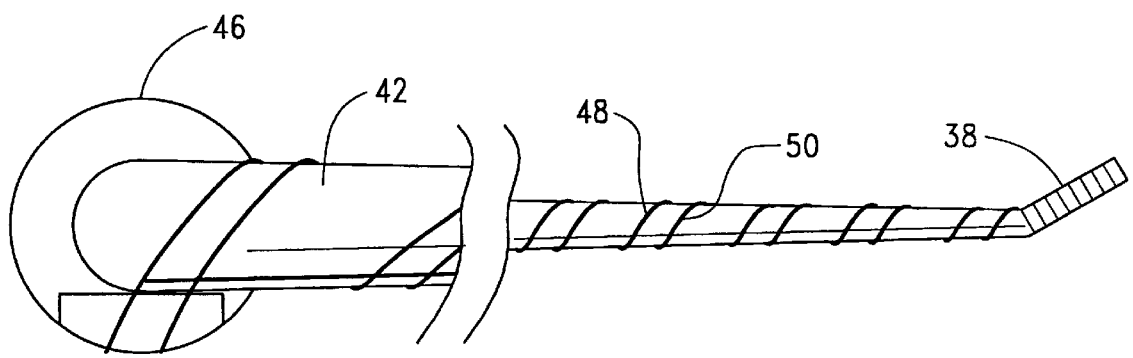
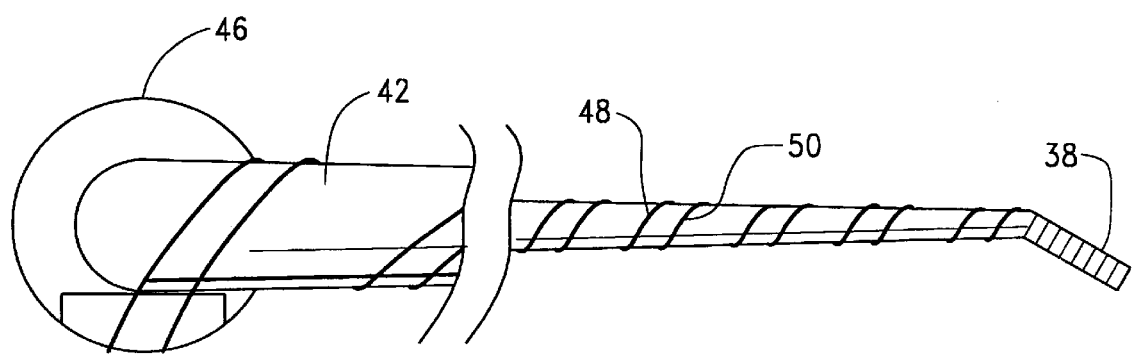

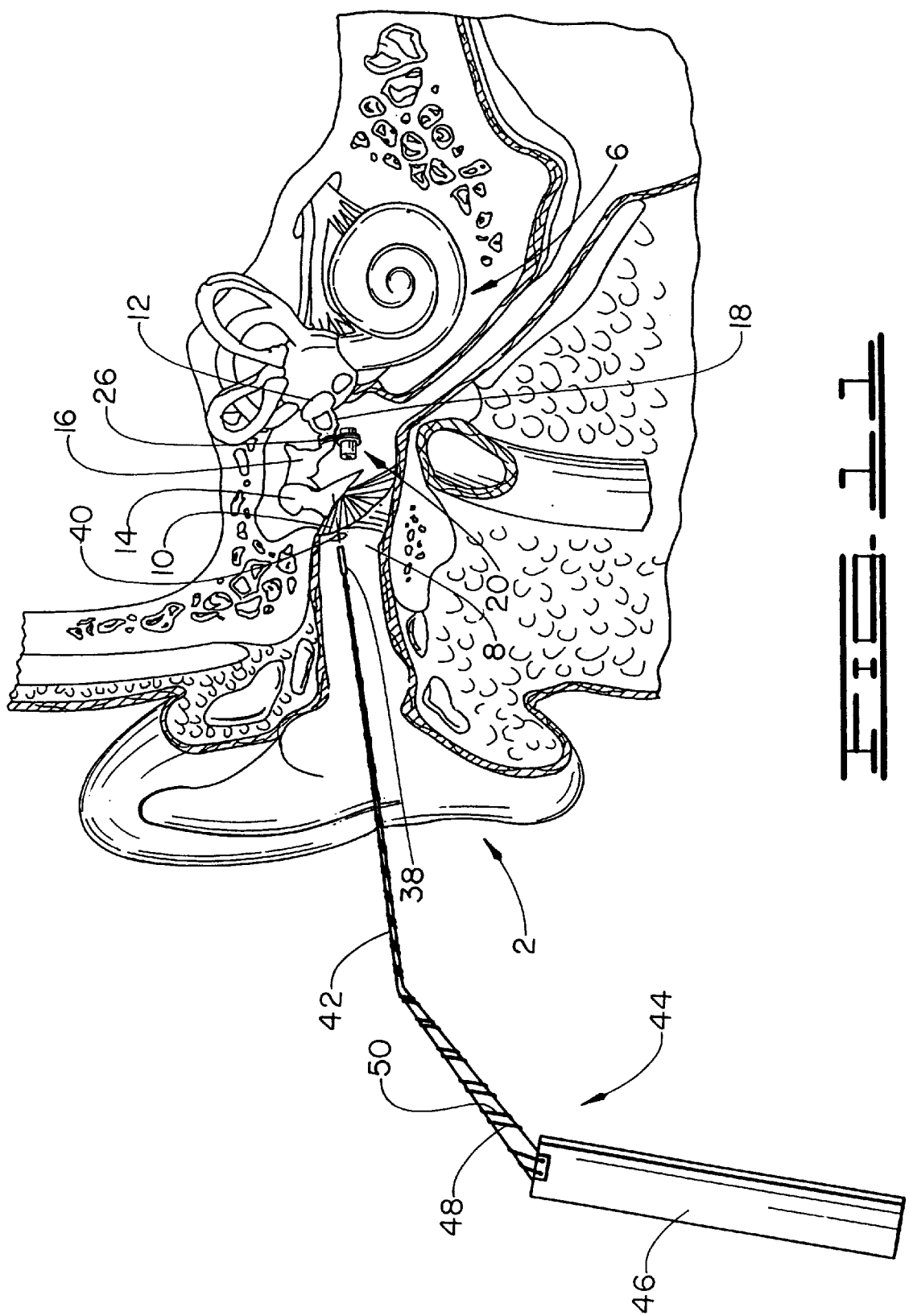

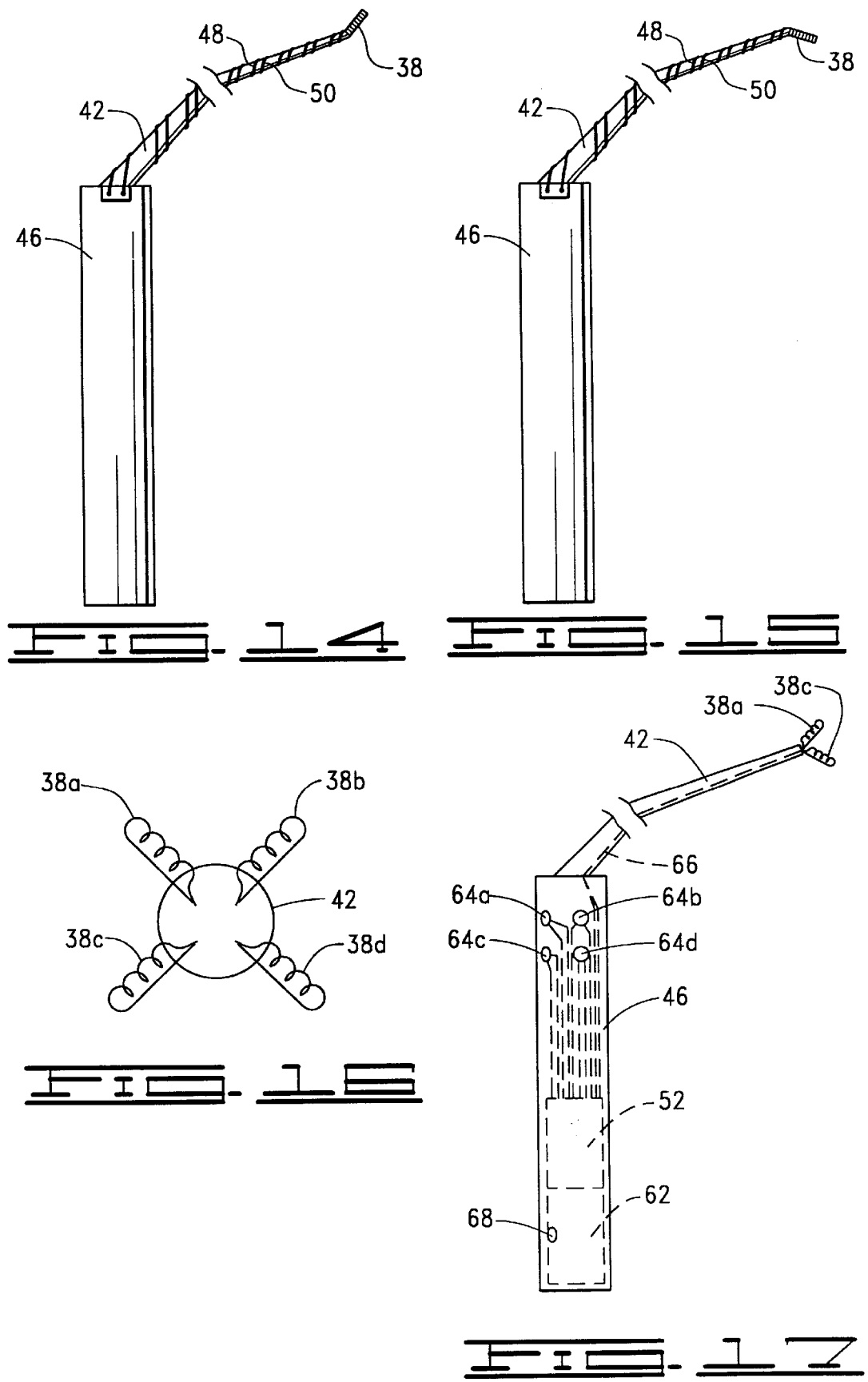

MIDDLE EAR MAGNET IMPLANT, ATTACHMENT DEVICE AND METHOD, AND TEST INSTRUMENT AND METHOD

BACKGROUND OF THE INVENTION

This invention relates generally to apparatus and methods used in or with magnetic middle ear hearing systems. The invention particularly relates to magnetic implants and to attachment devices and methods for mounting a magnet in a middle ear of a patient. The invention also particularly relates to test instruments and methods with which to locate or determine the orientation or operability of a magnet implanted in a middle ear.

There are many different reasons why some people have hearing impairment. In general, however, sound entering the outer ear canal does not get transmitted to the inner ear and/or transduced, then sent by auditory nerve. In some instances, this can be solved by amplifying the sound with a hearing aid put in the outer ear canal. In other cases, a device that electrically stimulates the auditory nerve directly needs to be implanted in the cochlea of the inner ear. In still other situations, a middle ear device that creates mechanical vibrations is needed. The present invention pertains to such middle ear devices, and specifically magnetic middle ear devices.

A person's normal middle ear includes a chain of small bones, or ossicles. The malleus, the incus, and the stapes form this chain; and when functioning normally, these ossicles transmit mechanical vibrations from the eardrum, or tympanic membrane, at the end of the outer ear canal to the oval window into the inner ear. When something is wrong in this ossicular chain, however, such transmission does not occur sufficiently to stimulate the cochlea and, therefore, auditory nerve. Alternatively, if transmission is normal but inner ear hair cells are damaged or absent, the auditory nerve is less activated. In both cases, greater amplitude of ossicular movement will correct the hearing deficit.

One general solution to hearing problems caused by middle ear deficiencies is to implant a magnet in the middle ear and to cause the magnet to vibrate in response to environmental sounds. The magnet is connected, for example, such that it provides mechanical vibrations to the oval window, either through an adequately functioning portion of the middle ear's ossicular chain to which the magnet is attached or through an implanted prosthesis carrying the magnet and communicating with the oval window.

A number of middle ear magnet attachment devices have been proposed. Some clip to an ossicle, or part of one; others abut ossicular surfaces. Shortcomings of these include clamping or clipping onto living bone (ossicles) with compromise of oxygen and nutrient delivery, wires attached to transducers adding mechanical loading, attaching probes connected to transducers wherein the probes must fit into holes placed into ossicles, gluing implants to living bone wherein the glue is not compatible with living bone and surface tension forces that seek to hold an implant onto the living epithelium of the round window of the inner ear. Additionally, I am not aware of any type of magnetic middle ear device which includes a narrow, completely closed loop that slides over a portion of the ossicular chain. Thus, there is the need for an attachment device and method, as well as an overall implant, which overcomes these shortcomings.

Regardless of the particular implant or mounting technique used for a middle ear magnet, problems can arise with regard to finding where the magnet is, determining what its particular magnetic orientation is, and checking that it is functional. These are significant at least in systems in which the magnet is remotely driven by an electromagnetic signal generated outside the middle ear. If the implanted magnet is not optimally aligned with an external coil from which the electromagnetic signal propagates, the implanted magnet might not respond adequately. Furthermore, some implanted magnets can become ineffective over time, so they need to be tested to see if they are the point of failure in a system that a patient reports has stopped functioning.

Changes in position and function of implanted magnets can occur from a variety of causes. For example, implant surgeons have different techniques and skills and thus magnet location may vary because of differences in surgeons. As another example, one particular type of attachment device might orient its magnet differently from how another particular type of attachment device orients its magnet even though the magnets are located at the same ossicular position in the respective patients. As a further example, anatomical differences between patients can cause similarly located magnets to be oriented differently relative to an external device (such as an external electromagnetic signal generating unit in the person's outer ear canal). Changes in orientation can also occur during the healing process following the implantation surgery (e.g., tissue growth touching the implant can alter its position). Still another example of change is that the functionality of an implanted magnet can deteriorate over time or as a result of leakage in the housing in which the magnet is typically located.

One significant consequence of location or orientation differences has to do with an audiologist's work related to the overall hearing assist system of the type in which an electromagnetic signal is generated and transmitted from outside the middle ear. Occasionally the unit that generates and transmits the signal is one molded to fit in the patient's outer ear canal. The audiologist makes the molded unit. If the audiologist does not know the location or orientation of the implanted magnet, typically the audiologist goes through an iterative process in which several molded units have to be made until the one that causes the implanted magnet to vibrate adequately is obtained. This is expensive, time consuming, and bothersome to the patient. Thus, there is the need for a test instrument and method with which to determine the location or orientation of the implanted magnet.

Another situation an audiologist can encounter is a patient who complains that a previously working system is no longer working. One component that could be malfunctioning is the implanted magnet. It could have become disoriented or dislodged, or its housing could have leaked such that the magnet does not function anymore. The magnet should not decay spontaneously, but it will decay if the housing leaks to body fluids. Such fluids will cause corrosion and the corroded magnet will lose its magnetism. Thus, there is the need for a test instrument and method with which to determine the operability of the implanted magnet.

SUMMARY OF THE INVENTION

The present invention overcomes the above-noted and other shortcomings of the prior art by providing a novel and improved implant and attachment device and method for mounting a magnet in a middle ear of a patient. The invention also provides a test instrument and method with which to locate or determine the orientation or operability of a magnet implanted in the middle ear.

The present invention facilitates implanting a magnet in a middle ear of a patient. It provides a general orientation at the location of implantation which preferably does not change during normal healing. The present invention allows for biologically compatible, non-necrotizing, light weight, anatomical positioning of a magnetic implant onto the ossicular chain. The chain is intact and blood supply/nutrient flow is maintained. Such mounting provides for lifetime implantation on an intact ossicular chain. Individual turns of a wire-form portion of this invention provide a scaffold for soft tissue to grow into and attach to, providing stability of the implant after healing has occurred. The wire-form attachment device is extremely light weight, thus minimizing loading of the ossicular chain and its mechanical movement.

The present invention, however, also enables the location of the magnet and its orientation to be confirmed or determined even after healing has occurred. The present invention can also be used to determine if the magnet and the whole system are functioning. That is, when a test coil of this invention is used to vibrate the implanted magnet, it serves to verify that the whole system is working because the subject will hear the vibration if it is working. With the present invention, differences in surgical techniques and skills and changes in location, orientation and function of implanted magnets can be accommodated by audiologists or others who make the external drive components (e.g., outer ear sound processors) or who work with the patients to make the hearing assist system work.

In one aspect, the present invention provides an attachment device for a middle ear implant. This attachment device is biocompatible and comprises: a first loop adapted to mount over a structure in a middle ear; and a second loop connected to the first loop and adapted to mount over an object for use in the middle ear. In a particular implementation, the first loop is disposed at an angle to the second loop. The attachment device is typically part of an implant for a middle ear. This implant which is another aspect of the present invention comprises: a housing; a magnet disposed in the housing; and the attachment device with the second loop disposed around the housing.

The present invention also provides a method of mounting an object in a middle ear. This method comprises sliding a loop along at least part of a middle ear ossicle or a prosthesis for a middle ear such that an object connected to the loop is disposed adjacent the ossicle or prosthesis. In a particular use, the method further comprises disconnecting the incus of the middle ear from the stapes of the middle ear and sliding the loop onto the stapes. This can further comprise reapposing the incus and the stapes, and applying a fibrin clot to the loop repositioned onto the reapposed incus and stapes. Preferably, the loop is positioned on the reapposed incus and stapes such that there is space between the body of the middle ear cavity and the object.

Another aspect of the present invention provides a method of testing for a magnet in a middle ear of a patient. This method comprises: inserting a coil at least into the patient's outer ear canal that is adjacent the middle ear having the magnet; selectably aiming the coil relative to the middle ear; driving the coil with an alternating current signal at each selected aiming; obtaining at least one indication in response to driving the coil with an alternating current signal at each selected aiming; and determining a functional or positional characteristic of the magnet from the obtained at least one indication. In a particular implementation, obtaining at least one indication includes obtaining at least one indication from the patient regarding whether sensations are perceived by the patient in response to driving the coil with an alternating current signal at each selected aiming and regarding the relative strengths of any such sensations.

This method can also be implemented with a plurality of coils. This method can be defined as comprising: inserting a plurality of coils at least into the patient's outer ear canal that is adjacent the middle ear having the magnet; driving each of the coils one at a time with an alternating current signal; obtaining at least one indication in response to driving each of the coils with an alternating current signal; and determining a functional or positional characteristic of the magnet from the obtained at least one indication.

The present invention also provides a test instrument for a magnet implanted in a middle ear of a patient. This test instrument comprises: at least one coil; and a handle connected to the at least one coil to enable a user of the test instrument to insert the at least one coil into at least an outer ear canal adjacent the middle ear of the patient and to direct electromagnetic signals at different directions relative to the middle ear. It can further comprise an oscillator connected to the at least one coil to generate the electromagnetic signals.

Therefore, from the foregoing, it is a general object of the present invention to provide a novel and improved implant and attachment device and method for mounting a magnet in a middle ear of a patient. Another general object of the present invention is to provide a novel and improved test instrument and method with which to locate or determine the orientation or operability of a magnet implanted in the middle ear. Other and further objects, features and advantages of the present invention will be readily apparent to those skilled in the art when the following description of the preferred embodiments is read in conjunction with the accompanying drawings.

BRIEF DESCRIPTION OF THE DRAWINGS

FIG. 2 is one side view of the preferred embodiment attachment device for a right ear.

FIG. 3 is another side view of the attachment device shown in FIG. 2.

FIG. 4 is an end view from above the orientation of the attachment device in FIG. 3.

FIG. 5 is a side view of the attachment device as oriented in FIG. 3 but with a magnet assembly retained in a lower loop portion of the attachment device.

FIG. 6 is one side view of the preferred embodiment attachment device for a left ear.

FIG. 7 is another side view of the attachment device shown in FIG. 6.

FIG. 8 is an end view from above the orientation of the attachment device in FIG. 7.

FIG. 9 is a side view of the attachment device as oriented in FIG. 7 but with a magnet assembly retained in the lower loop portion of the attachment device.

FIG. 10 is a sectional view of a magnet and housing of the magnet assembly held by the attachment devices as illustrated in FIGS. 1, 5 and 9.

FIG. 11 illustrates a preferred embodiment test instrument of the present invention in a test position in the outer ear canal of the depicted ear.

FIG. 12 is a top view of a preferred embodiment test instrument having a test coil leftwardly directed as viewed in FIG. 12 from the proximal, grip end of the test instrument.

FIG. 13 is a top view of a preferred embodiment test instrument having a test coil rightwardly directed as viewed in FIG. 13 from the proximal, grip end of the test instrument.

FIG. 14 is a side view of a preferred embodiment test instrument having a test coil upwardly directed as viewed in FIG. 14 from the proximal, grip end of the test instrument.

FIG. 15 is a side view of a preferred embodiment test instrument having a test coil downwardly directed as viewed in FIG. 15 from the proximal, grip end of the test instrument.

FIG. 16 illustrates a plural coil arrangement for another embodiment of the test instrument.

FIG. 17 is a side view of a preferred embodiment of the test instrument having the plurality of coils illustrated in FIG. 16.

DETAILED DESCRIPTION OF THE INVENTION

Figure 1:
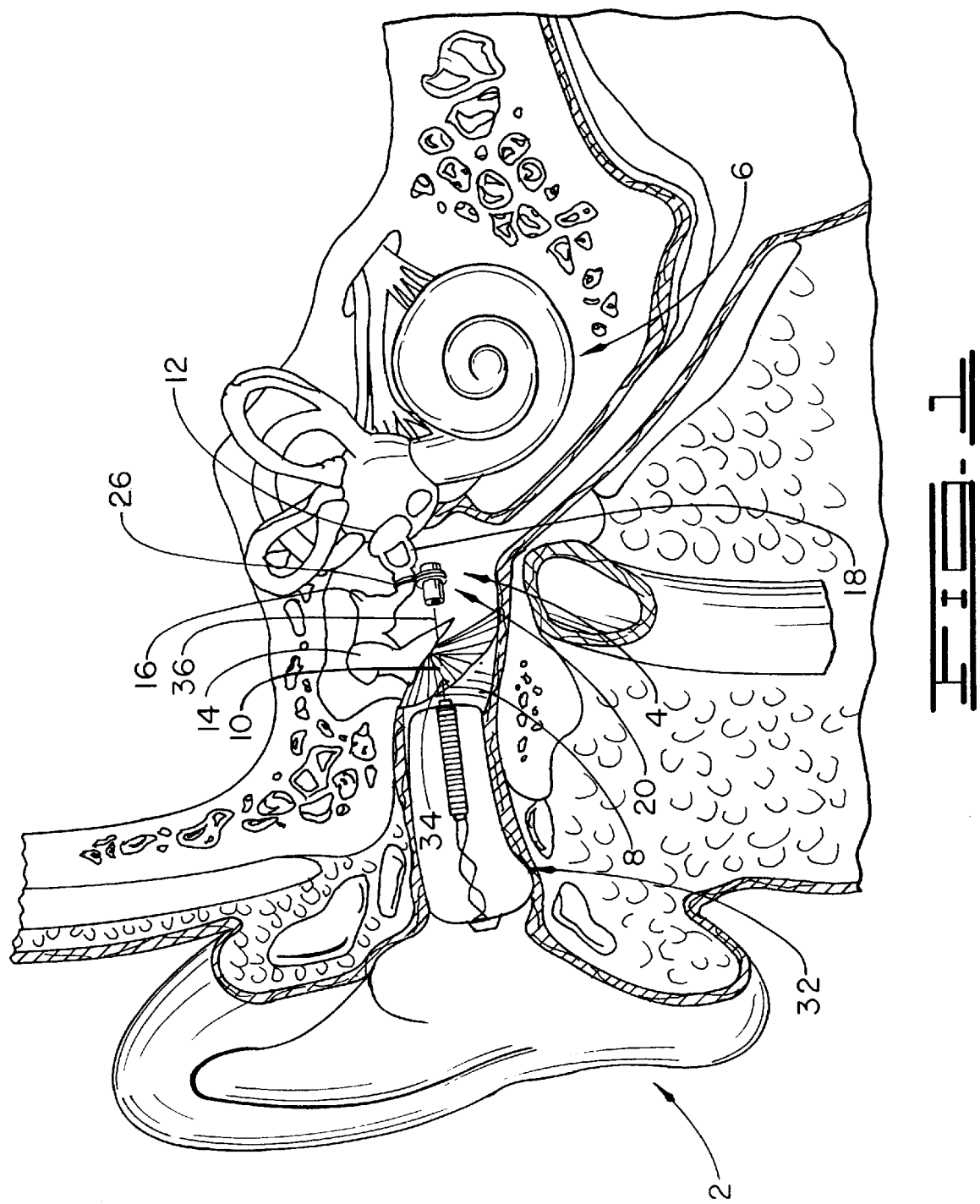
FIG. 1 is an illustration of portions of a human ear in which an attachment device of the present invention attaches a magnet to a portion of the ossicular chain.

A human ear is represented in FIG. 1. It includes an outer ear 2, a middle ear 4, and an inner ear 6. Pertinent to the description of the present invention is an outer ear canal 8 which is normally closed at its inner end by tympanic membrane, or eardrum, 10. Also pertinent is an ossicular chain, which if intact extends from tympanic membrane 10 to oval window 12 defining an entrance to the inner ear 6. The intact ossicular chain extends through the middle ear 4 and includes a malleus 14, an incus 16, and a stapes 18. A properly functioning ossicular chain transmits vibrations from the tympanic membrane 10 in series through the malleus 14, the incus 16 and the stapes 18 to the oval window 12. Vibrations at the oval window stimulate the inner ear 6 whereby the person perceives the sound received in the outer ear 2.

With regard to the present invention, it is assumed that the inner ear 6 responds to vibrations, or is made to respond, properly whereby a goal of the present invention is to provide the vibratory stimulation to the inner ear 6 when there otherwise is inadequate vibration transmission in the person's middle ear 4. To accomplish this, the present invention provides an implant 20 for a middle ear and especially an attachment device for a middle ear implant such as includes an object (e.g., a magnet) to be mounted in the middle ear by the attachment device.

Referring to FIGS. 1 and 10, the implant 20 includes a housing 22 and a magnet 24 disposed in the housing 22. In a particular implementation, the housing 22 is a commercially pure titanium canister, hermetically sealed and containing a rare earth permanent magnet (e.g., $Nd_2Fe_{14}B$) as the magnet 24. The lid of the canister is laser welded to the main body of the housing in an inert gas environment, excluding oxygen from the canister. A non-limiting example of the size of the illustrated housing 22 includes an outer length of nominally 2.362 millimeters (mm) ("nominally" as used throughout includes suitable engineering and manufacturing tolerances), an outer diameter of nominally 1.582 mm, an inner diameter of nominally 1.405 mm, and an inside depth of a cavity in the main body of the housing of nominally 2.254 mm. The magnet 24 for the housing 22 having these dimensions has a length of nominally 2.0 mm and a diameter of nominally 1.35 mm with a weight of approximately 0.02 gram (g) (these parameters include a parylene coating on the rare earth magnet). A lid for the housing's main body having the above dimensions has compatible inner and outer diameters (nominally 1.397 mm and nominally 1.549 mm) with an outer circumferential flange having a thickness of nominally 0.076 mm. A particular lid has a depression on its outer side of nominally 1.244 mm diameter, leaving a wall thickness of nominally 0.076 mm. Possible variations in the housing shape may be made to fit the implant according to and so as to accommodate the anatomical structures of the ossicles. Such variations in the housing may fit intraossicular, interossicular or paraossicular. Variations may include those other than the preferred embodiment of a right cylinder.

The preferred embodiment attachment device of the present invention for a right ear and as included in the illustrated implant 20 is generally identified in FIGS. 1–5 by the reference numeral 26. The preferred embodiment attachment device for a left ear is generally identified in FIGS. 6–9 by the reference numeral 26'. The attachment device 26 is described below, and the device 26' is marked with similar reference numerals since it is made the same except for the winding and angular orientations apparent from the drawings.

As illustrated in FIG. 1, the attachment device 26 connects the magnet 24, and its housing 22, to at least a partial middle ear ossicle. "At least a partial middle ear ossicle" means that the attachment device 26 mounts on a functional part of an ossicular chain, which could be less than the entire ossicular chain or less than a single ossicle. It can also be used with a complete ossicular chain, whether functioning normally or not. The present invention can also be used with a prosthesis for use in the middle ear in place of or instead of one or more parts of the ossicular chain. Thus, the present invention has general applicability to structure in the middle ear, whether such structure is natural or artificial.

The attachment device 26 includes two interconnected loops 28, 30. The loop 28 is adapted to mount around or over the selected ossicular portion or middle ear prosthesis. The illustrated particular implementation of the loop 28 includes three spaced turns of a biocompatible wire with an internal loop diameter of nominally 1.17 mm and axial length of nominally 0.6 mm (including two inter-turn spaces of nominally 0.075 mm). The wire is nominally 0.15 mm diameter and is contiguous with wire-form loop 30 which is an attachment mechanism to the implant housing 22. The preferred wire material is a biocompatible alloy of titanium, aluminum and vanadium (e.g., $TiAl_6V_4$).

The loop 30 is connected to the loop 28. The loop 30 is adapted to mount over the illustrated housing 22/magnet 24 assembly or another suitable transducer for use in the middle ear. As shown in the drawings, the loop 30 is disposed around the housing 22. This loop has a press fit around the housing 22 such that once the housing 22 is slid relative to the loop 30 to a desired position (such as nominally 0.2 mm from the lid-end of the housing 22 for the illustrated implementations), the compressive force of the loop 30 around the outside of the housing 22 retains the housing 22 in that position. This is illustrated in FIGS. 1, 5 and 9 for the illustrated embodiments.

The particular illustrated loop 30 includes four turns of a biocompatible wire with the internal loop diameter of nominally 1.44 mm and an axial length of nominally 0.6 mm (without spaces between adjacent turns). In this implementation, the wire is an extension of the wire used in the loop 28. The centers of the loops 28, 30 are vertically (as viewed in the drawings) spaced nominally 1.58 mm.

As apparent in FIGS. 2–5, the loops 28, 30 are disposed at an angle to each other. Although the loops 28, 30 are connected, the loops are not coplanar. Preferably, the loop 30 is at an angle to the loop 28 when the loop 28 is mounted over the ossicle such that an axial line to the magnet 24 (or the housing 22, or a line perpendicular to the plane of the loop 30) is aligned with a longitudinal line of the outer ear canal 8 adjacent the middle ear 4. More preferably, this line is aligned with a longitudinal axis of a transmission coil disposed in the outer ear canal 6. Such alignment optimizes the inductive coupling of the electromagnetic signal generated and transmitted with the transmission coil. Referring to FIG. 1, an electromagnetic coil and ear mold unit 32 is illustrated (the unit 32 does not form part of the claimed invention, and can be of any suitable type; this is, however, the component that an audiologist molds to any particular person/patient and thus it is preferable for the audiologist to know, before making the unit 32, the location and orientation of the implant 20 as referred to above). A longitudinal axis of the coil of the unit 32 is identified by the reference numeral 34. The respective aligned line through the housing/ magnet of implant 20 is identified in FIG. 1 by the reference numeral 36.

The angle between the axes of the loops 28, 30 in the illustrated implementation is nominally 30°. This has been selected based on anatomical studies performed on many fresh cadavers; however, other angles can be used as particular patient's anatomies or other experience or circumstances may dictate. Loops 28 and 30 are wound on known wire-form equipment using one continuous length of wire, and establishing the 30° offset. Variations in the present 30° (or other) angle can be determined by the surgeon's placement and fibrin clot fixation (described below) at the time of implementation.

The magnet 24, in its housing 22, is mounted in the middle ear 4 by sliding the loop 28 along at least part of a middle ear ossicle or a prosthesis for the middle ear such that the magnet 24, in its housing 22, is disposed adjacent to the ossicle or prosthesis. The loop 28 preferably is positioned on the ossicle or implanted prosthesis such that there is space between the magnet/housing and the body of the middle ear cavity. If the magnet/housing touches part of the body of the middle ear cavity, tissue may grow and attach to the exterior housing 22, which can alter the orientation of the magnet 24.

For the particular implementation illustrated in FIG. 1, a surgeon disconnects, by an appropriate technique known in the art (e.g., by surgically cutting), the incus 16 from the stapes 18 (such as at the incudostapedial joint). The surgeon slides the loop 28 over the cut joint and onto the stapes 18. The incus 16 and the stapes 18 are reapposed by natural spring forces. The surgeon positions the loop 28 on the joint between the incus 16 and stapes 18 such that there is space between structure of the middle ear and the housing 22 containing the magnet 24 (the implant 20 is preferably mounted on the incudostapedial joint or close to the oval window to reduce vibration conduction resistance). The surgeon also can apply a fibrin clot matrix including a gelatin sponge and blood mixture (e.g., a GELFOAM™ cast) to the loop on the ossicle(s). This facilitates positional healing (e.g., it helps prevent the loops from twisting about the joint).

More specifically, the placement of the implant 20 (housing 22, magnet 24 and attachment device 26) is made by first placing the implant into the middle ear cavity. A suture material (6-0) is placed under the incus 16 and passed outside the body so the surgeon can lift up the incus by pulling on the suture thread when the incudostapedial joint is cut. Next the joint is cut using a joint knife as commonly performed in standard stapedectomy procedures. The surgeon grasps the implant with non-magnetic forceps, lifts up on the incus so as to open the joint 0.6 mm to insert the loop 28 into the incudostapedial joint. Releasing the suture thread holding the incus 16 allows the spring forces of the ossicular chain to reappose the incus 16 and stapes 18 together. The implant is now approximately positioned for axial alignment with the electromagnetic coil to be placed in a subject's ear canal. Final alignment, visually performed by an implant surgeon, is done whereupon fixation of the implant and promotion of healing at the incudostapedial joint is accomplished by placing a gelatin-blood fibrin clot in and around loop 28 which is around the incudostapedial joint. This prevents the attachment device 26 from twisting about the joint.

The present invention also provides a method of testing for a magnet in a middle ear of a patient. This method can be used with what is described above or with other middle ear magnetic implants. It will, however, be described with reference to the implant 20.

Referring to FIG. 11, the method of testing for a magnet comprises: inserting a coil 38 (one or more as described below) at least into the patient's outer ear canal 8; selectably aiming the coil relative to the middle ear; driving the coil with an alternating current signal at each selected aiming; obtaining at least one indication in response to driving the coil with an alternating current signal at each selected aiming; and determining a functional or positional characteristic of the magnet from the obtained at least one indication. This can be accomplished with either a single coil or multiple coils of varying angles, shapes or morphology.

When using one coil, the coil 38 is inserted into the outer ear canal of the patient for the implementation shown in FIG. 11. The user, typically the surgeon during a postoperative examination (e.g., after an eight-week healing period), selectably aims the coil 38 within the outer ear canal 8 toward different locations of the middle ear 4. Typically this includes aiming the coil 38 at different regions of the tympanic membrane 10 at the end of the outer ear canal 8. For example, the coil 38 can be aimed at each of four quadrants (e.g., superior posterior, superior anterior, inferior posterior, inferior anterior) of the tympanic membrane 10.

With the coil aimed as desired, the coil is driven with an alternating current signal at each of the aimed locations. The alternating current signal is provided by any suitable source, one example of which is an oscillator as described below.

In response to driving the coil with an alternating current signal, at least one indication is obtained. For example, the patient responds regarding the relative strengths of sensations perceived by the patient due to the driven coil at each of the aimed locations. Of course if no response is given, meaning the patient has not perceived any sensations, then this indicates something is not functioning properly. Thus the indications from the patient include an indication regarding whether sensations are perceived by the patient in response to driving the coil with an alternating current signal at each selected aiming and, if sensations are perceived, regarding the relative strengths of such sensations.

Additionally, if the coil is activated by a particular known frequency, the sensitivity of the inner ear can be tested for that frequency. That is, any sensorineural, frequency-specific pathology of the inner ear can be evaluated by using the coil as a tuned testing device.

When indications of relative strength are given, the method further comprises determining a location of the magnet from the obtained indication(s). For example, if the coil was aimed at each of four quadrants of the tympanic membrane, the magnet is determined to be along the direction towards the quadrant of the tympanic membrane for which the patient gave an indication of the strongest vibratory (hearing) response. Thus, this is selected as the optimal location of the magnet.

Although the magnet is generally located by the foregoing, the orientation of the magnet at this location needs to be determined to assist the audiologist in making the outer ear canal unit 32, for example. The foregoing steps are repeated except that the aiming occurs at different angles relative to the determined general location of the magnet. In particular, the method further includes selectably aiming the coil within the outer ear canal 8 at different angles towards the determined location of the magnet. For the example regarding aiming relative to the tympanic membrane 10, this includes selectably aiming the coil at different angles towards the selected region (the specific quadrant if four quadrant regions are used) of the tympanic membrane where the location of the magnet was determined to be. The aimed coil is driven with an alternating current signal at each of the aimed angles. The method further includes obtaining at least one indication regarding the relative strengths of sensations. For example, the patient indicates what is perceived in response to driving the coil with an alternating current signal at each of the aimed angles. From this or these indications, an orientation of the magnet is determined. With this orientation known, an audiologist can readily make and place the outer ear canal unit 32 without multiple units having to be built in an iterative trial-and-error process.

The foregoing method can also be performed using multiple coils. For example, four coils can be used, one for each tympanic quadrant referred to above (other numbers of coils can be used, provided there is sufficient working space within the outer ear canal). For this embodiment, the method includes inserting the plurality of coils into the outer ear canal of the patient adjacent the middle ear having the magnet. The plurality of coils are suitably disposed relative to each other. For example, each coil is disposed relative to the other coils such that each coil is aimed at a different respective region of the tympanic membrane 10 at the end of the outer ear canal. As another example, the plurality of coils can be disposed relative to each other such that each coil is aimed at a different respective angle towards a selected region of the tympanic membrane 10. The remainder of the method is the same as described above in that the coils are driven by an alternating current signal and at least one indication is obtained in response to driving each of the coils with an alternating current signal. When the indication is to be obtained from the patient, each coil is driven one at a time so that the patient can have distinct perceptions of each sensation resulting from the driven coil. One can then determine a functional or positional characteristic of the magnet from the obtained indication or indications.

The method described above for one or more coils in the outer ear canal can also be performed within the middle ear in the same manner as described above with regard to the outer ear canal. Thus, the coil or coils are inserted at least into the outer ear canal as they can also be inserted on into the middle ear if the tympanic membrane is suitably open. For example, the tympanic membrane is first cut at the annulus and reflected upward and laterally to permit a surgeon a view of the middle ear space. This standard tympanoplasty procedure is commonly performed to repair middle ears. The coil 38 or multiple coils can then be inserted through the opened eardrum and into the middle ear cavity. The additional visualization, through a microscope, of an implant, by a surgeon will enable better positioning of the coil(s) 38 to ascertain the best placement of the electromagnetic coil in the ear mold unit 32. The permanent alignment of the electromagnetic coil within the ear mold unit 32 may be aimed horizontally or superiorly or inferiorly or anteriorly or posteriorly.

Figures 18, 19:
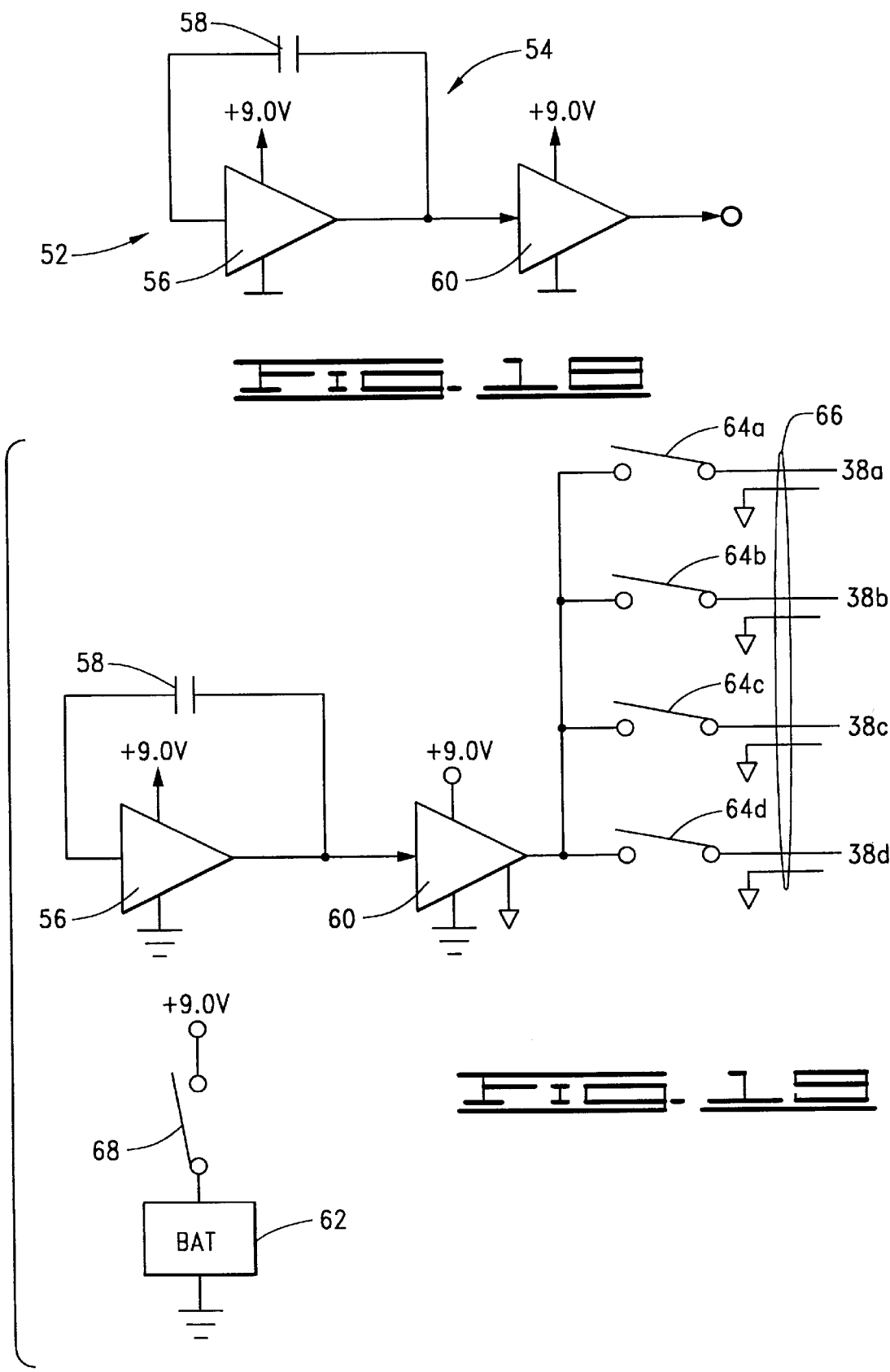
FIG. 18 is a schematic circuit diagram of an oscillator for the illustrated preferred embodiments of the test instrument.
FIG. 19 is a schematic circuit diagram of the oscillator with actuating switches such as for the configuration of FIGS. 16 and 17.

The testing method can be performed in any suitable manner; however, two general embodiments of a testing instrument that can be used are illustrated in FIGS. 11–18. Some versions of a single-coil embodiment are shown in FIGS. 11–15, and a multiple-coil (specifically four-coil) embodiment is shown in FIGS. 16 and 17. One embodiment of an oscillator for any of the implementations of FIGS. 11–17 is shown in FIG. 18.

Referring to FIGS. 11–15, the test instrument includes the coil 38. In a particular implementation, the coil 38 is nominally 1.5 mm in diameter, nominally 10.0 mm long, and comprised of AWG #43 copper wire wound on a core of nominally 1.0 mm×10.0 mm length mu metal. This particular coil has 327 turns, an inductance of 0.5 millihenries and a resistance of 9.2 ohms.

In the illustrated embodiment of FIG. 11, the coil 38 has a longitudinal axis 40 aligned with a shank 42 of a handle 44 of the test instrument. In another embodiment, the coil 38 can be aligned with the body 46 of the handle 44 if there is no angle in the instrument. The body 46 is that portion gripped by the user's hand. Left, right, up and down orientations of the coil 38 relative to the shank 42 and proximal, grip end (i.e., body 46 end) of the test instrument are depicted in FIGS. 12–15. Other orientations can be used. Additionally, other constructions can be used. For example, the coil 38 can be fixed at the end of the test instrument so that the coil 38 is at a fixed orientation; however, the coil 38 can also be movably mounted to the shank 42, such as with a ball joint. This latter configuration enables the surgeon or audiologist to selectably orient the coil 38 relative to the remainder of the test instrument.

In the illustrated embodiments, the shank 42 extends at an angle to the body 46 such that the user's hand, and the body 46 gripped by the hand, do not obstruct the user's vision when the distal end of the shank 42 and the coil 38 are inserted into the outer ear canal of the patient; however, other designs can be used so that broader aspects of the present invention are not limited to the specific body 46/shank 42 construction illustrated. That is, any suitable handle construction can be used, but preferably one that enables controlled placement or aiming of the coil 38 (or multiple coils) and visual inspection into the outer ear canal. In other words, whatever handle is used, it is connected to the coil or coils to enable the user to insert the coil(s) into at least the outer ear canal 8 and to direct electromagnetic signals at different directions relative to the middle ear.

In a particular implementation, the handle body 46 of the test instrument is composed of surgical grade stainless steel, approximately 8.0 centimeters (cm) in length, approximately 5.0 mm in diameter. The body 46 is connected with the shank 42 which is either hollow containing wires 48, 50 to the coil 38 or solid stainless steel whereby the wires from the coil 38 run along the outside of shank 42. The shank is bent or otherwise angled at approximately 45° with a distal length of approximately 8.0 cm and a proximal length of approximately 4.0 cm. Shank 42 has a nominally 4.0 mm diameter proximally and tapers to a nominally 1.0 mm diameter distally where the coil 38 is attached. In this implementation, the core of the coil 38 is epoxy glued to the shank 42.

In the illustrated embodiment, wires 48, 50 (either continuous from the coil 38 or separate wires connected to the coil 38) extend along the shank 42 or within a hollow shank and are connected to it by epoxy or coil Q dope. In a particular implementation, the wires 48, 50 are terminated at the handle body 46 in a #0604 female connector. A #92 male connector for two wires can connect with wires 48, 50 and communicate a suitable stimulation current from a separate oscillator (a non-limiting example is a two kilohertz alternating current signal having a variable amplitude up to a safe limit (and as limited by the power source)). Alternatively, an oscillator 52 can be built into the body 46 along with a battery power supply and one or more control switches (see FIG. 17). Another embodiment is to connect wires 48, 50 to a commercial function generator capable of producing a spectrum of sinusoidal waveforms to be transduced by coil 38 into electromagnetic energy.

Whatever oscillator is used, it provides an alternating current signal to the coil 38 via the wires 48, 50 such that electromagnetic signals are generated and transmitted from the coil 38. A particular implementation of the oscillator 52 is represented in FIG. 18. It includes an oscillating circuit 54 comprising an ULTIMA II linear mini hybrid, part no. 90836–000, from Resistance Technology, Inc., Arden Hills, Minn. (identified by reference numeral 56 in FIG. 18). The oscillating circuit 54 also includes a capacitor 58 (e.g., a chip capacitor of 270 picofarads for oscillation in the range of 1.8 kilohertz to 2.2 kilohertz) connected between the input and output of device 56. A Class D amplifier, part no. CD-3418, from Knowles Electronics, Inc., Itasca, Ill. (identified by reference numeral 60 in FIG. 18) interfaces the driving or stimulating signal to the wires 48, 50. Power for this particular implementation is nine volts, such as provided by a power supply 62 (FIG. 17) including six AAA batteries. These components can be installed in the handle body as illustrated in FIG. 17.

Continuing with FIG. 17, as well as FIG. 16, these drawings illustrate a particular multiple-coil embodiment of the test instrument. A plurality of coils 38a, 38b, 38c, 38d (in this particular example) are disposed at different angles to the shank 42 of the handle 44. These can be disposed to aim at (i.e., have their respective axial lines aligned with or pointed at) different quadrants of the tympanic membrane when the instrument is inserted into the outer ear canal 8. One alternative disposition of the coils 38a–38d is to aim them at different angles relative to a single region of the tympanic membrane. Each coil 38a–38d of one particular implementation is composed of 327 turns of AWG 43 copper wire on a nominally 1.0 mm core composed of mu metal. Each core and coil assembly is differentially aligned with respect to the long axis of shank 42. The four core/coil assemblies are connected to shank 42 by epoxy glue, whereupon angles of alignment are established. Coils 38a–38d may be individually aligned superiorly, inferiorly, posteriorly or anteriorly or axially with the long axis of shank 42. One configuration is to position four coils collectively in the left, right, up, down positions of FIGS. 12–15. The configuration of FIGS. 16 and 17 offsets the four coils from such four positions so that each coil 38 is directed to a respective one of the superior posterior, superior anterior, inferior posterior, and inferior anterior quadrants of the tympanic member when the handle body 46 is generally in a vertical position. This same orientation of the coils 38a–38d can be obtained with the first-mentioned implementation simply by rotating the handle relative to the tympanic membrane (or the second-described implementation can be rotated to match the orientation of the first-described implementation). Other dispositions of the coils 38 relative to the handle 44 can also be used. This includes embodiments directing the multiple coils at different angles relative to a particular sector (e.g., a particular quadrant of the tympanic membrane).

The embodiment of FIGS. 16 and 17 is otherwise the same as the embodiments of FIGS. 11–15 other than the oscillator being controllable to drive each coil in a selected manner. For the implementation illustrated in FIG. 17, four push-button switches 64a, 64b, 64c, 64d are mounted on the body 46 of the handle 44. Each of these switches 64 is connected to the oscillator 52 such that when actuated, the respective switch 64 connects the oscillator's driving signal to the respective coil 38, each such coil 38 connected by a respective pair of wires grouped in a cable 66 for the FIG. 17 implementation (see also FIG. 19). In this way, the user of the instrument can selectably energize each coil 38 after a master on/off switch 68 is turned on. For example, once the surgeon has positioned the quad-coil test instrument into a patient's ear canal and the switch 68 is turned on, then the surgeon can independently activate each coil 38a–38d by respective push button 64, asking the patient to identify the optimal (audible) response. When this is performed for the final angular orientation test and such optimal response is subjectively identified, then that coil 38 is identified to the audiologist as to the preferable angle in which to place the permanent coil in the ear mold assembly.

The test instrument of the present invention can also be inserted through the outer ear canal such that the coil(s) 38 are in the middle ear. Typically this is done after the tympanic membrane has been surgically opened to admit the coil-end of the instrument. Such surgery is done in any suitable manner (one example of which is described above).

Accordingly, from the foregoing the test instrument can be used intraoperatively, in a sterile manner, on a sedated but otherwise conscious patient. The test instrument thus is useful in informing the surgeon after implantation that the implant system is working, that the patient receives adequate stimulation, that the axis of orientation of the implant is sensorially optimum and that the magnet is fully magnetized.

Thus, the present invention is well adapted to carry out the objects and attain the ends and advantages mentioned above as well as those inherent therein. While preferred embodiments of the invention have been described for the purpose of this disclosure, changes in the construction and arrangement of parts and the performance of steps can be made by those skilled in the art, which changes are encompassed within the spirit of this invention as defined by the appended claims.

What is claimed is:

1. Attachment device for electromagnetically responsive middle ear implant, comprising:

a first loop configured to mount onto a natural or prosthetic ossicular structure in a middle ear; and a second loop connected to the first loop and configured to mount over an electromagnetically responsive object to mechanically vibrate in response within the middle ear to an electromagnetic signal, wherein the second loop is configured to be at an angle to the first loop when the first loop is mounted in the middle ear such that a perpendicular line through the second loop is aligned with a longitudinal line of an ear canal adjacent the middle ear.

2. Attachment device for electromagnetically responsive middle ear implant, comprising:

a first loop configured to mount onto a natural or prosthetic ossicular structure in a middle ear; and a second loop connected to the first loop and configured to mount over an electromagnetically responsive object to mechanically vibrate in response within the middle ear to an electromagnetic signal, wherein the second loop is configured to be at an angle to the first loop when the first loop is mounted in the middle ear such that a perpendicular line through the second loop is aligned with a longitudinal axis of a transmission coil disposed in an ear canal adjacent the middle ear.

3. A middle ear implant that creates mechanical vibrations in response to electromagnetic signals, comprising:
   a housing configured to be disposed in a middle ear;
   a magnet disposed and configured to be in the housing; and
   an attachment device configured to connect the housing to at least a partial middle ear ossicle or a prosthesis for the middle ear, the attachment device including:
      a first loop configured to mount around the at least partial middle ear ossicle or the prosthesis; and
      a second loop connected to the first loop and disposed around the housing such that the magnet in the housing is oriented to be responsive to electromagnetic signals transmitted into the middle ear when the housing is disposed therein on the attachment device, whereby mechanical vibrations are created, and such that the mechanical vibrations are transmitted to the at least partial middle ear ossicle or prosthesis when the first loop is mounted therearound, wherein the second loop is configured to be at an angle to the first loop when the first loop is mounted over the ossicle such that an axial line through the magnet is substantially aligned with a longitudinal line of an ear canal adjacent the middle ear.

4. A middle ear implant that creates mechanical vibrations in response to electromagnetic signals, comprising:
   a housing configured to be disposed in a middle ear;
   a magnet disposed and configured to be in the housing; and
   an attachment device configured to connect the housing to at least a partial middle ear ossicle or a prosthesis for the middle ear, the attachment device including:
      a first loop configured to mount around the at least partial middle ear ossicle or the prosthesis; and
      a second loop connected to the first loop and disposed around the housing such that the magnet in the housing is oriented to be responsive to electromagnetic signals transmitted into the middle ear when the housing is disposed therein on the attachment device, whereby mechanical vibrations are created, and such that the mechanical vibrations are transmitted to the at least partial middle ear ossicle or prosthesis when the first loop is mounted therearound, wherein the second loop is configured to be at an angle to the first loop when the first loop is mounted over the ossicle such that an axial line through the magnet is substantially aligned with a longitudinal axis of a transmission coil disposed in an ear canal adjacent the middle ear.

5. A middle ear implant that creates mechanical vibrations in response to electromagnetic signals, comprising:
   a housing configured to be disposed in a middle ear;
   a magnet disposed and configured to be in the housing; and
   an attachment device configured to connect the housing to at least a partial middle ear ossicle or a prosthesis for the middle ear, the attachment device including:
      a first loop configured to mount around the at least partial middle ear ossicle or the prosthesis; and
      a second loop connected to the first loop and disposed around the housing such that the magnet in the housing is oriented to be responsive to electromagnetic signals transmitted into the middle ear when the housing is disposed therein on the attachment device, whereby mechanical vibrations are created, and such that the mechanical vibrations are transmitted to the at least partial middle ear ossicle or prosthesis when the first loop is mounted therearound;
      wherein the first loop includes a wire segment disposed in three spaced turns, and wherein the second loop includes a respective wire segment disposed in four turns, the respective wire segment continuous with the wire segment of the first loop.

6. An implant as defined in claim 5, wherein the first loop is disposed at an angle to the second loop.

7. An implant as defined in claim 6, wherein the angle is about 30° defined between respective axial lines of the first and second loops.

8. Attachment device for middle ear implant that includes a magnet-containing housing and that increases amplitude of movement of at least a natural, living ossicular portion communicating with an oval window into an inner ear, the attachment device comprising:
   a first multiple-turn wire loop that mounts on the natural living ossicular portion, wherein turns of the first loop are spaced and provide a scaffold for soft tissue of the ossicular portion to grow into and attach to, thereby stabilizing the attachment device on the ossicular portion after the first loop is mounted thereon; and
   a second multiple-turn wire loop connected to the first loop to hold the magnet-containing housing within the second loop, wherein the second loop has a constrictive effect that provides a press-fit onto the magnet-containing housing so that the magnet-containing housing does not move independently from the ossicular portion when the attachment device and the magnet-containing housing are mounted thereon;
   wherein the first loop and the second loop are angularly disposed relative to each other such that the first loop is configured to mount on an incudostapedial joint.

9. Attachment device as defined in claim 8, wherein the second loop is configured to axially align with an electromagnetic coil placed in an adjacent ear canal.

10. Attachment device for electromagnetically responsive middle ear implant, comprising:
    a first coiled-wire loop configured to mount on natural or prosthetic ossicular structure in a middle ear;
    a second coiled-wire loop connected to the first loop and configured to hold a transducer;
    wherein the first loop and the second loop are angularly disposed relative to each other such that the first loop is for mounting on an incudostapedial joint; and
    wherein in response to mounting the first loop on the incudostapedial joint the second loop axially aligns with an electromagnetic coil placed in an adjacent ear canal.

11. Attachment device for electromagnetically responsive middle ear implant, consisting of:
    a first loop for mounting over natural or prosthetic ossicular structure in a middle ear;
    a second loop connected to the first loop for holding a transducer;
    wherein the first loop and the second loop are angularly disposed relative to each other such that the first loop mounts on an incudostapedial joint; and
    wherein the second loop axially aligns with an electromagnetic coil placed in an adjacent ear canal when the first loop mounts on the incudostapedial joint.

12. Attachment device for electromagnetically responsive middle ear implant, comprising:

first coiled-wire loop means for mounting on an incudostapedial joint; and second coiled-wire loop means, connected adjacent the first loop means, for holding an electromagnetically responsive object for use in responding within the middle ear to an electromagnetic signal to provide mechanical vibrations.

13. Attachment device as defined in claim 12, wherein the first coiled-wire loop means and the second coiled-wire loop means are angularly disposed relative to each other such that the second coiled-wire loop means axially aligns with an electromagnetic coil placed in an adjacent ear canal when the first coiled-wire loop means is on the incudostapedial joint.

14. An implant for a middle ear, comprising:

a housing;

a magnet disposed in the housing; and an attachment device for connecting the housing to at least a partial middle ear ossicle or a prosthesis for the middle ear, the attachment device consisting of:

a first loop configured to mount around the at least partial middle ear ossicle or the prosthesis; and a second loop connected adjacent the first loop and disposed around the housing, wherein the first loop and the second loop are angularly disposed relative to each other such that the first loop mounts on an incudostapedial joint and in response thereto the second loop axially aligns with an electromagnetic coil placed in an adjacent ear canal.

15. An implant for a middle ear, comprising:

a rare earth permanent magnet;

a titanium canister containing the magnet, the canister having a main body and a lid welded to the main body in an inert gas environment; and a biocompatible wire forming two loops, including a first loop configured to mount on a selected ossicular portion or middle ear prosthesis and further including a second loop receiving the canister.

16. An implant as defined in claim 15, wherein the first loop and the second loop are angularly disposed relative to each other such that the first loop mounts on an incudostapedial joint and the second loop axially aligns the titanium canister containing the magnet with an electromagnetic coil placed in an adjacent ear canal.

17. An implant as defined in claim 15, wherein:

the magnet has a length of nominally 2.0 millimeters and a diameter of nominally 1.35 millimeters;

the canister has an outer length of nominally 2.362 millimeters and an outer diameter of nominally 1.582 millimeters;

the first loop includes three turns of the biocompatible wire defining an internal loop diameter of nominally 1.17 millimeters and an axial length of nominally 0.6 millimeter; and the second loop includes four turns of the biocompatible wire defining an internal loop diameter of nominally 1.44 millimeters and an axial length of nominally 0.6 millimeter.

\* \* \* \* \*

UNITED STATES PATENT AND TRADEMARK OFFICE
CERTIFICATE OF CORRECTION

| | |
|---|---|
| PATENT NO. | : 6,277,148 B1 |
| DATED | : August 21, 2001 |
| INVENTOR(S) | : Kenneth J. Dormer |

It is certified that error appears in the above-identified patent and that said Letters Patent is hereby corrected as shown below:

<u>Title page,</u>
OTHER PUBLICATIONS, A. Tjellström et al. reference, third line, delete "1993" and insert -- 1983 -- therefor.

<u>Column 12,</u>
Line 64, delete "car" and insert -- ear -- therefor.

<u>Column 13,</u>
Line 1, delete "car" and insert -- ear -- therefor.
Line 6, delete "car" and insert -- ear -- therefor.

<u>Column 14,</u>
Line 66, delete "car" and insert -- ear -- therefor.

<u>Column 16,</u>
Line 11, delete "arc" and insert -- are -- therefor.

Signed and Sealed this

Nineteenth Day of March, 2002

Attest:

JAMES E. ROGAN
Director of the United States Patent and Trademark Office

Attesting Officer